United States Patent [19]
Jia

[11] Patent Number: 5,902,825
[45] Date of Patent: May 11, 1999

[54] COMPOSITION AND METHOD FOR THE PALLIATION OF PAIN ASSOCIATED WITH DISEASES OF THE BONE AND BONE JOINTS

[75] Inventor: Wei Jia, Columbia, Mo.

[73] Assignee: Mitreoak, Ltd., Columbia, Mo.

[21] Appl. No.: 08/779,719

[22] Filed: Jan. 7, 1997

[51] Int. Cl.$^6$ .................................................. A01N 55/02
[52] U.S. Cl. .......................... 514/492; 514/493; 424/604; 534/15; 556/1; 556/13; 556/18
[58] Field of Search .................................. 556/1, 13, 18; 534/15; 514/492, 493; 424/604

[56] References Cited

U.S. PATENT DOCUMENTS

| | | | |
|---|---|---|---|
| 4,426,384 | 1/1984 | Wyburn-Mason | 424/253 |
| 4,680,286 | 7/1987 | Stockel et al. | 514/23 |
| 4,704,273 | 11/1987 | McMichael | 424/85 |
| 4,725,622 | 2/1988 | Nelson et al. | 514/469 |
| 4,906,450 | 3/1990 | Lieberman et al. | 424/1.1 |
| 5,352,676 | 10/1994 | Doria et al. | 514/237.5 |

OTHER PUBLICATIONS

Biodistribution of Sn–117m(4+)DTPA for Palliative Therapy of Painful Osseous Metastases[1] ;By Dr. Atkins et al; *Radiology Magazine*, vol. 186, No. 1, Jan. 1993. Pp. 279–283.

Samarium–153–PHYP; By Clunie et al; *The Journal of Nuclear Medicine*, vol. 36, No. 1, Jan. 1995. Pp. 51–57.

Drug therapy reviews: Antirheumatic agents; By Ronald P. Evens; *American Journal of Hospital Pharmacy*, vol. 36, May 1979. Pp. 622–633.

Coordination Compounds in Nuclear Medicine; By S. Jurisson et al; *Chemical Reviews*, vol.93, No.3, 1993. Pp. 1137–1156.

Bone Metastases; By Rubens and Fogelman; *The Systemic of Bone Metastases*. Pp. 132–138.

Textbook of Radiopharmacy; By Charles B. Sampson; *Nuclear Medicine*, vol. 3. Pp. 32–35.

An Evaluation of Tc–Labeled . . . ; By Gopal Subramanian, Ph.D, et al; *Radiopharmaceuticals*. Pp. 319–328.

The Development and In–Vivo . . . ; By S.C. Srivastava et al; *Int. J. Nucl. Med. Biol.*, vol. 12, No. 3, 1985, pp. 174–184.

Chemical Abstracts, vol. 68, Chem. Abs. No. 90386, 1966.

Chemical Abstracts, vol. 75, Che. Abs. No. 133605, 1971.

Chemical Abstracts, vol. 109, Chem Abs. No. 157413, 1988.

Nash et al., Inorganic Chemistry, vol. 34, pp. 2753–2758, 1995.

Chemical Abstracts, vol. 123, abstract No. 242919, 1994.

Spiess et al., Polyhedron, vol. 6, No. 6, pp. 1247–1249, 1987.

*Primary Examiner*—Porfirio Nazario-Gonzalez
*Attorney, Agent, or Firm*—Shook, Hardy & Bacon LLP

[57] ABSTRACT

A therapeutic composition and method of using the same for the palliation or relief of pain in patients having diseases which affect the bone and bone joints including metastatic bone cancer, arthritis, and other inflammatory arthropathies. The therapeutic composition comprises as the active agent a complex formed of non-radioactive metal ions and organic phosphonic acid ligands, or pharmaceutically acceptable salts thereof.

30 Claims, No Drawings

COMPOSITION AND METHOD FOR THE PALLIATION OF PAIN ASSOCIATED WITH DISEASES OF THE BONE AND BONE JOINTS

FIELD OF THE INVENTION

The present invention relates generally to the field of therapeutic pharmaceuticals, and is more specifically directed to a composition and method of using the same for the palliation of pain in patients having diseases affecting the bone and bone joints including metastatic bone cancer, rheumatic diseases such as rheumatoid arthritis, osteoarthritis and other inflammatory arthropathies.

BACKGROUND OF THE INVENTION

Various forms and types of disease are known to negatively affect and damage the bones and bone joints of humans and animals. Typically these diseases cause severe and often chronic pain which increases over time eventually progressing to result in loss of function and/or destruction of the joints of the body. The source of this pain and joint damage varies depending upon the disease.

For instance, osteoarthritis is a common degenerative joint disorder which normally affects older persons. Osteoarthritis is marked by inflammation of the joint causing swelling, pain and stiffness reducing the mobility and activity of the patient. These symptoms increase in intensity and regularity with advancing age. The constant inflammation can eventually lead to complete or partial loss of function and damage to the larger weight-bearing joints of the body.

The rheumatic diseases, particularly rheumatoid arthritis, juvenile rheumatoid arthritis and psoriatic arthritis are also marked by chronic inflammation primarily of the synovial tissue leading to pannus formation and eventual destruction of the articular cartilage. In addition to inflammation problems, these diseases also cause the release of various enzymes including collagenase and lysosomal enzymes in the affected area. These enzymes act to indiscriminately destroy extra-cellular collagen fibers and ultimately destroy the connective tissue surrounding the joints.

Another relatively common disease known to affect the bone is metastatic bone cancer which often times accompanies primary cancers in other tissues, notably the lung, breast, and prostate. This form of cancer causes abnormal cell activity in bone, resulting in severe pain and consequent immobility, anorexia, and the need for long-term narcotic analgesia. More specifically, this disease is often associated with overactive osteoblasts (cells which are normally associated with new bone growth) in the bone which cause excessive bone growth in the area of the cancer. Alternatively, the disease may cause abnormally high osteoclastic activity (osteoclasts are cells normally associated with bone resorption) in bone resulting in the destruction of the bone material. Those individuals having excessive osteoclastic activity may also suffer from a condition known as hypercalcaemia caused by excessive levels of calcium ions in the blood resulting from the bone being dissolved or destroyed at an increased rate.

Osteoarthritis, the rheumatic diseases, metastatic bone cancer and other less common forms of inflammatory arthropathies affect great numbers of people in the United States. The cost of treatment and care combined with loss of work time and productivity is incalculable. For instance, it is estimated that one to three percent of the population in the United States is afflicted with rheumatoid arthritis with more than half of these patients suffering inflammation and eventual destruction of the hand and knee joints. With an increasing survival time in the population, these diseases constitute one of the greatest medical, social, and economic problems existing today.

Successful treatment of these diseases generally focuses on pain relief, reduction of inflammation, and preservation of the remaining functional capacity of joints and the adjoining muscles. While complete resolution of the pathological process (e.g. a cure) has not been found, successful early treatment particularly in the case of rheumatoid and osteoarthritis may avert the destructive, deforming phase of the disease.

Presently, the primary method of treating the rheumatoid diseases and arthritis is by drug therapy using anti-inflammatory compounds directed at blocking or reducing synovial inflammation thereby improving function and analgesics directed to reducing pain. Aspirin and other salicylate compounds are frequently used in treatment to interrupt amplification of the inflammatory process and temporarily relieve the pain. Other drug compounds used for these purposes include phenylpropionic acid derivatives such as Ibuprofen and Naproxin, Sulindac, phenyl butazone, corticosteroids, antimalarials such as chloroquine and hydroxychloroquine sulfate, and fenemates. For a thorough review of various drugs utilized in treating rheumatic diseases, reference is made to *J. Hosp. Pharm.,* 36:622 (May 1979).

While these known drug therapies have utility, there are drawbacks to their use. For instance, it may take up to six months of consistent use of some of these medications in order for the product to have effect in relieving the patient's pain. Consequently if the product doesn't work for that particular patient, it could take up to six months before the physician is able to accurately make that assessment. Many of these drugs also cause serious side effects in certain patients, and therefore the patient should be carefully monitored to assure that these side effects are not unduly threatening. Most of these drugs bring only temporary relief to the patient and therefore must be taken consistently on a daily or weekly basis for continued relief. As the disease progresses, the amount of medicant needed to alleviate the pain may increase to relatively high daily doses. The potential for adverse side effects consequently increases with higher dosage amounts. To further complicate matters, many of these patients suffer from other conditions which require them to take a variety of different medications, increasing the risk of negative side effects and interaction between drugs.

Some treatments not only reduce the amount of inflammation and pain, but actually slow the progression of the disease or joint destruction. For instance, gold salts such as gold sodium thiomalate, aurothioglucose, and other sources of auric and aurous ions are said to produce a favorable response in about 75 percent of patients with actual disease remission in 20–25 percent. One major drawback to the use of gold therapy is that the gold is distributed via the blood system not only to the diseased joint, but to a number of tissues in the body including the liver, skin, bone, bone marrow, eyes, and reticuloendothelial system. The gold often causes serious adverse reactions in these tissues including dermatitis, nephrotoxicity, blood dyscrasias and ocular toxicity. A certain amount of the gold also binds with humoral or cellular components such as serum albumin making the bound gold unavailable for purposes of treatment.

Since only a percentage of the total amount of gold administered is actually delivered to the diseased site, significantly high doses of the compound are required for effective treatment. Yet, the risk of adverse reactions is only exacerbated and more pronounced, in certain circumstances becoming life threatening, by virtue of the large dosage amounts administered. It is known to reduce the toxic effects of gold therapy by use of a selenium-containing compound. (U.S. Pat. No. 4,680,286 to Stockel, et al.). However, the amount of gold required for treatment and delivered to the various organs of the body is not reduced using this detoxification method, the selenium is merely provided to expedite elimination of the gold from those organs which can be most severely negatively affected such as the renal system and liver.

A relatively new method of treating rheumatoid arthritis which is also believed to actually slow the progression of the disease is the use of D-penicillamine, a natural metabolite of penicillin. Like many of the other drugs used in the past, penicillamine has drawbacks because it is relatively slow-acting requiring 8–12 weeks of use before it can be determined whether the patient is responding. Penicillamine can also cause several adverse effects and can be toxic in some patients.

Where the inflammation is present in larger joints such as the knee for example, an alternative to drug therapy is the surgical incision of the inflamed synovium using a procedure known as surgical synovectomy. In this procedure the inflamed synovium and pannus formation are surgically removed which tends to relieve the pain and in many cases proves to arrest the disease. In order to avoid the risks of surgery it is also known to destroy the diseased synovium by a procedure known as radiation synovectomy. Radiation synovectomy consist of injecting a radionuclide directly into the articular region affected whereby the radiation kills the diseased tissue to abate the inflamed synovium. Known methods of radiation synovectomy include intra-articular injection of $^{121}$Sn hydroxide in a carrier (See, U.S. Pat. No. 4,906,450 to Lieberman, et al.) and $^{153}$Sm labeled particulate hydroxyapatite (citation).

Radionuclides have also been delivered to the affected area by the use of bone seeking carriers or agents. For instance, the use of β-emitting radionuclides $^{186}$Re and $^{153}$Sm complexed with phosphonates have been suggested for relieving pain in patients with metastatic bone cancer. (See, *Coordination Compounds in Nuclear Medicine*, Chem. Rev. 1993, 93, 1137–1156, 1148). Phosphonates were initially shown to have a high affinity for sites of actively growing bone when used in skeletal or bone imaging. Di-phosphonate products have also been used for the treatment of various diseases associated with bone joint pain and destruction. For example, 3-amino-1-hydroxypropylidene 1-di-phosphonate commercially available as Pamidronate from Ciba Geigy is known to reduce the pain of abnormal bone turnover known to exist in Paget's Disease (a disease with the symptoms of marked pain and stiffness of bone and joints). Another di-phosphonate product known as Clodronate (di-chloromethane di-phosphonate) and commercially available from Boerhinger has been found to reduce pain and damage in patients having extensive destruction of the lumbar spine. The di-phosphonates have also been used as resorption inhibitors for the treatment of malignant hypercalcaemia associated with overactive osteoclasts. (See *Bone Metastases*, R. D. Rubins and I. Fogelman, Springer-Verlag London Ltd. 1991).

In a recent study of radionuclide complexes used for radiotherapy in bone tumors, complexes of $^{117m}$Sn with the ligands of pyrophosphate, phosphonate, anddiethylene-triaminepentaacetid acid (DTPA) were prepared. The investigators reported that the $^{117m}$Sn-DTPA complex was best suited for radiotherapy and that the tin compound itself acted as a bone-localizing agent having a tendency for high bone uptake. See, e.g. *Int. J. Nucl. Med. Biol.*, Vol. 12, No. 3, pp. 167–174 (1985); see also, *Radiology*, Vol. 186, No. 1 pp. 279–283 (1993).

Thus, the two methods that have primarily been suggested for radiotherapy are articular injection whereby the material is directly injected into the joint for treatment, or i.v. injection whereby the radionuclide complexed with a ligand such as phosphonate is injected intravenously and rapidly localized to the skeleton. While these methods of application attempt to distribute the radionuclide only to the affected area, studies have indicated that activity is leaked or distributed to other parts of the body even when using these techniques. The major drawbacks of these radiotherapeutic agents are the relatively low bone lesion uptake and undesirably high radiation dose to normal tissues. The other problem involved in the preparation of these radiotherapeutic agents is the lack of availability of the radionuclides. Radionuclides are produced from a nuclear reactor or an accelerator Currently there are very few of the radionuclide production facilities operating in the world, which have seriously limited the availability of the medical radionuclides. Furthermore, many radionuclides are either difficult to produce, such as $^{117m}$Sn, which can only be produced from a high flux reactor, or too short-lived to be shipped throughout the country, such as $^{121}$Sn (27 hours). As a result, there are very few radiodiagnostic and radiotherapeutic bone agents that have been approved by the United States Food and Drug Administration.

While the rheumatoid diseases, osteoarthritis, metastatic bone cancer and other crippling arthropathies differ somewhat as to source and symptoms, there are certain factors common to each. Firstly, the disease causes chronic or severe pain which significantly impairs the quality of life for the patients. Secondly, the disease, when advanced, causes bone destruction and/or abnormal bone growth. Thirdly, while various forms of drug therapy have been developed for treating these conditions, none have proven successful without continued dosing and/or unwanted side effects. In addition, the drug may be distributed throughout many parts of the body causing toxic side effects in the skin, the liver, the urinary tract and other vital organs. Fourthly, while various forms of radiotreatment have been developed to destroy diseased tissue and/or reduce pain, these treatments involve the use of potentially harmful radioactive materials in the body, are relatively expensive and not easily adapted for convenient use in many doctors' offices or clinics. Thus, there remains a need in the art to develop new methods of treatment to reduce the pain experienced by these patients, and to reduce or prevent joint destruction with minimal negative side effects to the patient.

Thus, a primary object of the present invention is to provide a composition and method for the palliation of pain in patients with metastatic bone cancer, arthritis, or other inflammatory arthropathies which does not require the use of a radionuclide or other radioactive material.

Another object of the present invention is to provide a composition and method for the palliation of pain in patients with metastatic bone cancer, arthritis, or other inflammatory arthropathies wherein the active therapeutic agent is administered to the patient in relatively low dosage amounts.

A further object of the present invention is to provide a composition and method for the palliation of pain in patients with metastatic bone cancer, arthritis, or other inflammatory arthropathies which not only relieves the pain associated with the disease, but also inhibits and/or prevents further destruction of the diseased tissue.

Another object of the present invention is to provide a composition and method for the palliation of pain in patients with metastatic bone cancer, arthritis, or other inflammatory arthropathies wherein the active therapeutic agent is selectively delivered to the bone and bone joints, and specifically to those areas of tissue affected by the disease.

A further object of the present invention is to provide a composition and method for the palliation of pain in patients with metastatic bone cancer, arthritis, or other inflammatory arthropathies wherein single treatments are effective for relatively long term pain relief without the need for daily and/or weekly administration.

A further object of the present invention is to provide a composition and method for the palliation of pain in patients with metastatic bone cancer, arthritis, or other inflammatory arthropathies wherein pain relief and prevention of further tissue damage can be achieved through the administration of small dosage amounts which are effective for extended periods of time.

A further object of the present invention is to provide a composition and method for the palliation of pain in patients with metastatic bone cancer, arthritis, or other inflammatory arthropathies wherein the active therapeutic agent is selectively delivered to the diseased areas providing immediate pain relief as well as relatively long term prevention of tissue destruction by blocking the inflammatory process and/or inhibiting osteoblastic or osteoclastic overactivity.

SUMMARY OF THE INVENTION

These and other objects are achieved by a therapeutic composition and method of using the same for the palliation or relief of pain in patients having diseases which affect the bone and bone joints including metastatic bone cancer, arthritis, and other inflammatory arthropathies. The therapeutic composition comprises as the active agent a complex formed of metal ions and organic phosphonic acid ligands, or pharmaceutically acceptable salts thereof, wherein the metal ions used are those which carry a relatively high formal charge of +3 or greater and tend to form insoluble phosphate complexes. When administered into the body, the metal ion—phosphonate complex is selectively distributed to the skeletal system and more specifically to those areas affected by disease such as in areas of synovial inflammation, bone resorption, or osteoblastic overactivity.

This selective distribution is believed attributable to the high affinity that phosphonates have for the hydroxyapatite surface of the bone with enhanced deposition in regenerating bone. The phosphonates are known to be resistant against attack by biological enzymes such as phosphatase. Thus, the highly charged metal ions complexed with the phosphonates are selectively transported to the area of the disease and are prevented from binding with other humoral or cellular components due to the chelation of the phosphanate ligands.

While the specific mechanism has not been verified, it is believed that once the complex reaches the diseased tissue, phosphate ions present on the surface of the bone replace the phosphonate ligands and form a very stable complex with the metal ion. The metal phosphate complexes form a precipitate layer on the bone surface. The freed phosphonates then interact with components in the bone lesion sites similar to how the known di-phosphonate products of Edidronate, Clodronate and Pamidronate behave to temporarily inhibit abnormal cellular activity and relieve pain.

While the phosphonates are believed to provide only temporary relief before degradation, the metal ion phosphate precipitate layer formed on the bone surface is extremely stable and not subject to degradation. This relatively insoluble precipitate layer is believed to interfere or block bone resorption caused by enzymes or abnormal osteoclastic cell activity, osteoblastic overactivity, as well as inflammation within the joint region and on the bone surface. The inorganic precipitate of metal ion and phosphate is therefor believed to act as a palliative agent and also as an agent for preventing further destruction of the bone. Since the metal ion phosphate complex is extremely stable and secured to the bone surface as a precipitate, it will remain for a long period of time providing therapeutic relief for extended periods.

DETAILED DESCRIPTION OF THE INVENTION

The therapeutic composition of the present invention comprises an active agent complex formed of a metal ion and an organic phosphonic acid ligand, or a pharmaceutically acceptable salt thereof, wherein the metal ion is not radioactive and has a relatively high charge of +3 or greater. It is believed that in vivo at the bone lesion sites, the phosphonates are bound to the surface of hydroxaptite through calcium metal in the bone matrix. The metal ion forms a relatively insoluble stable complex with phosphate ions present on the bone surface, which forms a precipitate layer on the surface of the bone. This layer is believed to block or interfere with bone resorption, osteoblastic activity and inflammation to relieve pain and joint destruction long term.

The metal ion to be used in accordance with this invention must be capable of forming stable complexes with organic phosphonates and of forming stable complexes with phosphate on the bone surface. Metal ions meeting these requirements form basic oxides and carry a relatively high formal charge of +3 or greater. Particularly suitable metal ions tend to form insoluble phosphates or hydroxides and thus are insoluble and immobile in vivo meaning that they exist as a precipitate on the bone surface for extended periods of time. Specific metal ions preferred for purposes of this invention are selected from the group consisting of Gallium III ($Ga^{+3}$), Tin IV ($Sn^{+4}$), Indium III ($In^{+3}$), and all Lanthanides in the series including Samarium III ($SM^{+3}$), and Cerium III ($Ce^{+3}$). Gallium III ($Ga^{+3}$) and Tin IV ($Sn^{+4}$) are most preferred insofar as both of these metal ions have been used and approved for various uses in the body. For example, tin has been used in a number of different radiopharmaceuticals such as for skeletal imaging. A gallium nitrate product has been used in the treatment of tumor induced hypercalcaemia.

The metal ion is complexed with an excess amount of organic phosphonic acids, or the pharmaceutically acceptable salts thereof. Particularly suitable organic phosphonic acids for purposes of the present invention are selected from the group consisting of organic di-phosphonic acids, triphosphonic acids, tetra-phosphonic acids and mixtures thereof. Suitable di-phosphonic acids include ethylenehydroxy-diphosphonic acid (EHDP), methylenediphosphonic acid (MDP), and aminoethyl-diphosphonic acid (ADEP). Suitable triphosphonic acids include nitrilotri-(methylene)-phosphonic acid (NTP) and aminotrismethylene-phosphonic acid (AMP). Tetra-phosphonic acids suitable for purposes of this invention include ethylenediaminetetramethylene-phosphonic acid (EDTMP), nitrilotri-methylene phosphonic acid (NTMP), tetraazacyclododecanetetramethylene phosphonic acid (DOTMP), and diethylene-triaminepetnamethylene phosphonic acid (DTPMP).

The most preferred phosphonic acids for purposes of this invention include methylenediphosphonic acid (MDP), ethylenehydroxydiphosphonic acid (EHDP), and ethylenediaminetetramethylene-phosphonic acid (EDTMP), and tetraazacyclododecanetetramethylene phosphonic acid (DOTMP) having the formulas:

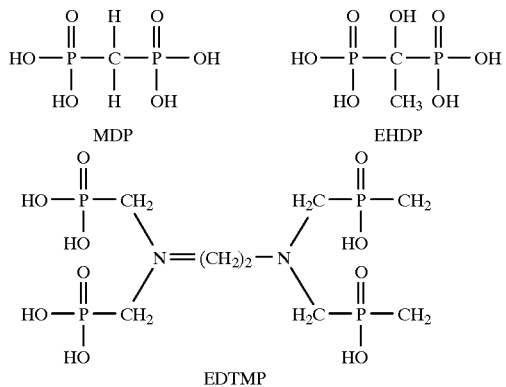

Most of the phosphonate ligands are commercially available in the acid form or may be readily prepared by methods known to those skilled in the art. Depending upon the metal ion being complexed, the phosphonates may alternatively be converted or obtained as a base addition salt in order to provide a pH environment which is more conducive to formation of the complex with the ions. Any pharmaceutically acceptable cation may be used to prepare these salts provided the cation is chosen to retain the biological effectiveness and properties of the corresponding free acid. Suitable cations for binding with the acid ligands may be selected from the group derived from inorganic bases including sodium, potassium, lithium, ammonium, calcium, and magnesium, or from organic bases including primary, secondary, and tertiary amines. Most preferred bases in accordance with this invention comprise sodium hydroxide, potassium hydroxide, potassium carbonate, sodium carbonate and magnesium carbonate.

While the inventors believe that any number of different metal ion phosphonate complexes meeting the above criteria can be used for purposes of the present invention, the most preferred complexes are selected from the group consisting of Sn(IV)-MDP, Sn(IV)-EDTMP, Sn (IV)DOTMP, and Ga(III)-EHDP.

Compositions comprising these complexes as the active agent may be used in treating metastatic bone cancer, rheumatoid diseases, osteoarthritis and other forms of inflammatory arthropathies by administering a therapeutically effective amount of the complex to the human or animal in need. Administration of the active compounds can be affected via any medically acceptable mode of administration for agents which control inflammation and associated pain. These methods include, but are not limited to, oral, parenteral including subcutaneous, sublingual, intravenous and intra-articular injection and other known methods of systemic administration.

In a preferred method of making the complex, the phosphonic acid, or pharmaceutically acceptable salt thereof, is fully dissolved in a solvent selected from the group consisting of water, aqueous alcohols, glycols, phosphonate esters or carbonate esters to provide a dissolved phosphonate solution. Optionally a base may be added and/or the solution may be heated to fully dissolve the phosphonates in solution. The concentration of phosphonates in solution will vary depending upon the amount of metal ion intended to be complexed and the solubility of the phosphonate. In general, it is preferred that the phosphonate concentration in the dissolved solution range from 0.5 to 15 percent by weight and preferably from 2 to 7 percent by weight.

To insure that all of the metal ion present in the composition is complexed, it is preferable to use an excessive amount of ligand in preparing the complex in accordance with this invention. In this manner the phosphonate ligand will completely surround or encompass the metal ions to prevent the metal ion from being absorbed into the soft tissue and to prevent the metal ion from bonding with other humoral or cellular components during transport to the affected areas. The metal ion, normally in the form of a metal salt, is therefore added to at least a 2 to 50 fold molar excess of the dissolved phosphonate, preferably to a 3 to 20 fold molar excess of the dissolved phosphonate, to form the complex.

Once the complex is formed, the resulting complex solution is then adjusted to a biologically acceptable pH ranging from a pH of 4 to 8, and preferably a pH of 6 to 7 by the addition of a base such as sodium hydroxide. The pH adjusted complex solution may then be further processed to provide the complex in a form suitable for administration.

The complex may be incorporated into any pharmaceutically acceptable dosage forms in conventional manner including tablets, suppositories, pills, capsules, powders, liquids, suspensions, emulsions, and the like. The dosage form will generally include a pharmaceutically acceptable excipient, the active complex and may additionally include other medicinal agents, pharmaceutical agents, carriers, adjuvants or stabilizers which enhance the therapeutic effectiveness of the composition and/or facilitate easier administration of the composition.

In preparing solid dosage forms, the complex may be incorporated with non-toxic solid carriers such as pharmaceutical grades of mannitol, Sorbitol, lactose, starch, magnesium stearate, sodium saccharin, the polyalkylene glycols, talcum, cellulose glucose, sucrose, and magnesium carbonate, cyclodextrin and the like; binding agents such as cellulose, methylcellulose, hydroxy-propylcellulose, hydroxy-propylmethylcellulose, polyvinyl pyrollidone, gelatine, gum arabic, polyethylene glycol, white sugar, starch and the like; disintegrators such as starch, carboxy-methylcellulose, calcium salts of carboxy-methylcellulose and the like; lubricants such as talc and the like; and/or preservatives such as sodium benzoate, sodium bisulfite and the like.

Liquid dispersions for oral administration such as syrups, emulsions and suspensions will generally include the complex in a carrier such as saccharose or saccharose with glycerine, mannitol, sorbitol, a natural gum, agar, sodium alginate, pectin, methylcellulose, carboxy-methylcellulose, and/or polyvinyl alcohol.

In preparing liquid solutions for intravenous or intra-articular injections, the complex is preferably sterile filtered into an injection bottle having a suitable carrier such as sterile water or preferably sterile aqueous isotonic saline solutions.

If desired, the therapeutic composition to be administered may also contain minor amounts of nontoxic auxiliary substrates such as wetting or emulsifying agents, pH buffering agents and the like. Typical examples of such axillary agents are sodium acetate, sortiban monolaurate, triethanolamine sodium acetate, triethanolamine oleate, etc.

The therapeutic composition of the present invention will, in any event, contain a quantity of the active agent complex in an amount effective to alleviate the symptoms. The therapeutic regiment for the different clinical syndromes must be adapted to the type of pathology taking into account the route of administration, the form in which the complex is administered and the age, weight and conditions of the subject involved. Taking into consideration the foregoing, doses of the active complex will broadly range from about 0.2–5 mg complex per kg of body weight. Of course, these dosage regimens may be adjusted to provide the optimal therapeutic response.

The following examples are for purposes of illustrating a suitable method of making complexes in accordance with this invention and are not intended to be limiting as to the method employed for making the complex or the components used for making the complex.

EXAMPLE I

A Sn(IV)-MDP complex was formed by mixing 25 mg of $SnCl_2 \cdot H_2O$ (containing 13.15 mg of Sn) with 97 mg of $Na_2MDP$ in a reaction vial containing 5 ml of distilled water. The pH of the resulting solution was adjusted to a pH of 9 to 10 by addition of NaOH. The resulting solution was heated to between 80°–90° C. for 10 minutes About 1 ml of 30% $H_2O_2$ was added after cooling and the sample was reheated in a boiling water bath for 5 minutes. The pH of the solution was then adjusted to 7–8 by addition of HCl. The volume of solution was adjusted to 10 ml using physiological saline. The molar ratio of metal to ligand (Sn:MDP) in the complex is ~1:4.

EXAMPLE II

In the preparation of a Sn(IV)-EDTMP complex, the stannous chloride, $SnCl_2 \cdot H_2O$, was dissolved in a 1 N HCl solution and then added to a 3-fold molar excess (with respect to tin) of the sodium salt of EDTMP. While stirring, NaOH was added to the mixture until a clear solution was obtained. A 1:1 molar amount of $CaCl_2 \cdot 2H_2O$ (based on EDTMP) was added and NaOH was added dropwise until the white precipitate disappeared. The preparation was heated at 100° C. for 10 minutes to insure complexation. A 2-fold equivalent excess of 30% $H_2O_2O$ was added after cooling and the solution was reheated in a boiling water bath for 5 minutes. The final pH was adjusted to ~8.5 using HCl.

From the foregoing it will be seen that this invention is one well adapted to attain all ends and objects hereinabove set forth together with the other advantages which are obvious and which are inherent to the structure.

It will be understood that certain features and subcombinations are of utility and may be employed without reference to other features and subcombinations. This is contemplated by and is within the scope of the claims.

What is claimed is:

1. A composition for the palliation of pain in patients, said composition comprising a therapeutically effective amount of a complex of a non-radioactive metal ion selected from the group consisting of Gallium III ($Ga^{+3}$), Tin IV ($Sn^{+4}$), Indium III ($In^{+3}$), Samarium III ($Sm^{+3}$) and Cerium III ($Ce^{+3}$) and a phosphonate compound selected from the group consisting of phosphonic acid and pharmaceutically acceptable salts thereof, and a carrier for said complex.

2. A composition for the palliation of pain in patients having diseases of the bone and/or bone joints said composition comprising a therapeutically effective amount of a complex of a non-radioactive metal ion with a charge of +3 or greater and a phosphonate compound, said metal ion is selected from a group consisting of metal ions capable of forming a complex with said phosphonate compounds and forming a water insoluble complexes with phosphate ions, wherein said metal ion is selected from the group consisting of Gallium III ($Ga^{+3}$) and Tin IV ($Sn^{+4}$), said phosphonate compounds being selected from the group consisting of phosphonic acid and pharmaceutically acceptable salts thereof.

3. A composition in accordance with claim 1, wherein said phosphonic acid is selected from the group consisting of organic di-phosphonic acids, triphosphonic acids, tetraphosphonic acids, tetraaminophosphonic acids and mixtures thereof.

4. A composition for the palliation of pain in patients having diseases of the bone and/or bone joints, said composition comprising a therapeutically effective amount of a complex of a non-radioactive metal ion selected from the group consisting of Gallium III ($Ga^{+3}$), Tin IV ($Sn^{+4}$), Indium III ($In^{+3}$), Samarium III ($Sm^{+3}$) and Cerium III ($Ce^{+3}$) and a phosphonate compound selected from the group consisting of phosphonic acid and pharmaceutically acceptable salts thereof, said phosphonic acid being selected from the group consisting of organic di-phosphonic acids, tri-phosphonic acids, tetra-phosphonic acids, tetraaminophosphonic acids, and mixtures thereof, wherein said di-phosphonic acids are selected from the group consisting of ethylenehydroxydiphosphonic acid (EHDP), methylenediphosphonic acid (MDP), and aminoethyl-diphosphonic acid (ADEP), and mixtures thereof.

5. A composition in accordance with claim 3, wherein said triphosphonic acids are selected from the group consisting of nitrilotri-methylene-phosphonic acid (NTP) and aminotrismethylene-phosphonic acid (AMP), and mixtures thereof.

6. A composition in accordance with claim 3, wherein said tetra-phosphonic acids are selected from the group consisting of ethylenediaminetetramethylene-phosphonic acid (EDTMP), nitrilotri-methylene phosphonic acid (NTMP), tetraazacyclo-dodecanetetramethylene phosphonic acid (DOTMP), diethylene-triaminepetnamethylene phosphonic acid (DTPMP), and mixtures thereof.

7. A composition for the palliation of pain in patients having diseases of the bone and/or bone joints, said composition comprising a therapeutically effective amount of a complex of a non-radioactive metal ion and a phosphonate compound, wherein said composition is selected form the group consisting of Sn (IV)-MDP, Sn (IV)-EDTMP, Sn (IV)-DOTMP, and Ga (III)-EHDP.

8. A composition in accordance with claim 1, wherein said metal ion is complexed with an excess amount of said phosphonate compound.

9. A composition in accordance with claim 1, wherein said composition is administered in a therapeutically effective amount for the palliation of pain in patients having a disease selected from the group consisting of metastatic bone cancer, rheumatic disease, osteoarthritic, and other inflammatory arthropathies.

10. A method for the palliation of pain in a patient having a disease of the bone and/or bone joints, said method comprising:

administering to said patient a therapeutically effective amount of a composition comprising a complex of a non-radioactive metal ion and phosphonate compound, said phosphonate compound being selected from the group consisting of phosphonic acids and pharmaceutically acceptable salts thereof.

11. A method in accordance with claim 10, wherein said metal ion is selected from the group consisting of metal ions capable of forming a complex with said phosphonate compounds and of forming water insoluble complexes with phosphate ions.

12. A method in accordance with claim 11, wherein said metal ion is selected from the group consisting of ions having a charge of +3 or greater.

13. A method in accordance with claim 12, wherein said metal ion is selected from the group consisting of Gallium III ($Ga^{+3}$), Tin IV ($Sn^{+4}$), Indium III ($In^{+3}$), Samarium III ($Sm^{+3}$) and Cerium III ($Ce^{+3}$).

14. A composition in accordance with claim 13, wherein said metal ion is selected from the group consisting of Gallium III ($Ga^{+3}$) and Tin IV ($Sn^{+4}$).

15. A method in accordance with claim 10, wherein said phosphonic acid is selected from the group consisting of organic di-phosphonic acids, triphosphonic acids, tetraphosphonic acids and mixtures thereof.

16. A method in accordance with claim 10, wherein said composition is selected from the group consisting of $Sn^{+4}$-NDP, $Sn^{+4}$-EDTMP, and $Ga^{+3}$-HEDP.

17. A method for the palliation of pain associated with a disease of the bone and/or bone joint, said method comprising depositing a therapeutically effective amount of a precipitate layer of a metal ion-phosphate complex on the surface of the bone affected by the disease.

18. A composition comprising a therapeutically effective amount of a complex of a metal and a phosphonic acid, said metal selected from the group consisting of Sn (IV), Ga (III), and In (III), said phosphonic acid selected from the group consisting of ethylenediaminetetramethylenephosphnic acid (EDTMP), diethylenetriaminepentamethylenephosphonic acid (DTPMP), nitrilotrimethylenephosphonic acid (NTMP), tetraazacyclododecanetetramethylenephosphonic acid (DOTMP), methylenediphosphonic acid (MDP), hydroxyethylenediphosphonic acid (HEDP), aminoethyldiphosphonic acid (ADEP) and mixtures thereof.

19. A composition in accordance with claim 18 wherein the metal ion is Sn (IV).

20. A composition in accordance with claim 18 wherein the metal ion is Ga (III).

21. A composition in accordance with claim 18 wherein the metal ion is In (III).

22. A method in accordance with claim 10, wherein the phosphonate compound is a phosphonic acid or a physiologically acceptable salt thereof selected from the group consisting of:

ethylenediaminetetramethylenephosphonic acid (EDTMP), diethylenetriaminepentamethylenephosphonic acid (DTPMP), nitrilotrimethylenephosphonic acid (NTMP), tetraazacyclododecanetetramethylenephosphonic acid (DOTMP), methylenediphosphonic acid (MDP), hydroxyethylenediphosphonic acid (HEDP), aminoethyldiphosphonic acid (ADEP), and mixtures thereof.

23. A method in accordance with claim 10, wherein the phosphonate compound is selected from the group consisting of EDTMP, DTPMP, NTMP, and DOTMP; and the metal ion is selected from the group consisting of La, Ce, Pr, Nd, Pm, Sm, Eu, Gd, Tb, Dy, Ho, Er, Tm, Yb, Lu.

24. A method in accordance with claim 10, wherein the metal ion is Sn(IV) or Ga (III) and the phosphonate compound is selected from the group consisting of MDP, HEDP, ADEP, physiologically acceptable salts thereof, and mixtures thereof.

25. A method in accordance with claim 10, wherein said composition is selected from the group consisting of $Sn^{+4}$-MDP, $Sn^{+4}$-EDTMP, $Ga^{+3}$-HEDP, $Ga^{+3}$-EDTMP, $In^{+3}$-EDTMP, $SN^{+4}$-DTPMP, $Ga^{+3}$-DTPMP, $In^{+3}$-DTPDMP, $Sn^{+4}$-NTMP, $Ga^{+3}$-NTMP, $In^{+3}$-NTMP, $Sn^{+4}$-DOTMP, $Ga^{+3}$-DOTMP, $In^{+3}$-DOTMP, $Sn^{+4}$-HEDP, $Sn^{+4}$-ADEP, $Ga^{+3}$-MDP, $Ga^{+3}$-ADEP, physiologically acceptable salts thereof, and mixtures thereof.

26. A composition for the palliation of pain in patients, said composition including a pain palliative complex of a non-radioactive metal ion having a formal charge of at least +3 and a phosphonic acid component comprising at least one of phosphonic acid and a pharmaceutically acceptable salt of phosphonic acid, there being a sufficient amount of said phosphonic acid component present in the complex to prevent the metal ion from being absorbed into soft tissue or bonding with humoral or cellular components during transport of the complex to affected areas.

27. A medicinal dose for the palliation of pain in patients, said dose including a therapeutically effective amount of a pain palliative complex of a non-radioactive metal ion having a formal charge of at least +3 and a phosphonic acid component comprising at least one of phosphonic acid and a pharmaceutically acceptable salt of phosphonic acid, and a physiologically acceptable carrier for said complex.

28. A composition for the palliation of pain in patients, said composition comprising a pain palliative complex of a non-radioactive metal ion having a formal charge of at least +3 and a phosphonic acid component comprising at least one of phosphonic acid and a pharmaceutically acceptable salt thereof, and a physiologically acceptable carrier for said complex, said complex being present in said composition in a therapeutically effective amount relative to said carrier.

29. A composition for the palliation of pain in patients, said composition including a pain palliative complex of a non-radioactive metal ion having a formal charge of at least +3 and a phosphonic acid component comprising at least one of phosphonic acid and a pharmaceutically acceptable salt of phosphonic acid, there being a sufficient amount of said phosphonic acid component present in the complex to completely surround the metal ion.

30. A composition for the palliation of pain in patients, said composition including a pain palliative complex of a non-radioactive metal ion having a formal charge of at least +3 and a phosphonic acid component comprising at least one of phosphonic acid and a pharmaceutically acceptable salt of phosphonic acid, said complex being characterized by having been prepared in the presence of an excess of the phosphonic acid component relative to the metal ion.

* * * * *